(12) United States Patent
Elgaard et al.

(10) Patent No.: US 9,468,443 B2
(45) Date of Patent: Oct. 18, 2016

(54) OCCLUSION BALLOON

(71) Applicant: COOK MEDICAL TECHNOLOGIES LLC, Bloomington, IN (US)

(72) Inventors: Per Elgaard, Haslev (DK); Erik E. Rasmussen, Slagelse (DK); Edwin E. Macatangay, Bloomington, IN (US); Sarah Reeves, Cory, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 180 days.

(21) Appl. No.: 14/134,341

(22) Filed: Dec. 19, 2013

(65) Prior Publication Data

US 2014/0188153 A1    Jul. 3, 2014

Related U.S. Application Data

(60) Provisional application No. 61/746,324, filed on Dec. 27, 2012.

(51) Int. Cl.
*A61M 29/00* (2006.01)
*A61B 17/12* (2006.01)

(52) U.S. Cl.
CPC ... *A61B 17/12136* (2013.01); *A61B 17/12109* (2013.01); *A61B 2017/12095* (2013.01)

(58) Field of Classification Search
None
See application file for complete search history.

(56) References Cited

U.S. PATENT DOCUMENTS

| 3,834,394 | A | * | 9/1974 | Hunter | A61B 17/12031 604/907 |
| 4,327,734 | A | * | 5/1982 | White, Jr. | A61B 17/12109 604/907 |
| 4,364,392 | A | * | 12/1982 | Strother | A61B 17/0057 604/103.01 |
| 5,222,970 | A | | 6/1993 | Reeves | |
| 6,152,144 | A | | 11/2000 | Lesh et al. | |
| 7,632,291 | B2 | * | 12/2009 | Stephens | A61B 17/12022 606/195 |
| 8,366,734 | B2 | * | 2/2013 | Hardert | A61B 17/12136 606/195 |
| 8,439,890 | B2 | | 5/2013 | Beyar et al. | |
| 2010/0185233 | A1 | * | 7/2010 | Thommen | A61B 17/0057 606/213 |
| 2012/0259406 | A1 | | 10/2012 | Schreck et al. | |

FOREIGN PATENT DOCUMENTS

| EP | 2 319 455 A2 | 5/2011 |
| WO | 00/72781 A2 | 12/2000 |
| WO | 2006/114783 A2 | 11/2006 |

* cited by examiner

*Primary Examiner* — Tuan V Nguyen
(74) *Attorney, Agent, or Firm* — Brinks Gilson & Lione

(57) ABSTRACT

A delivery system for an occlusion balloon includes a delivery catheter and a balloon releasably detached thereto. The balloon can include a base portion that is threaded onto the end of the delivery catheter. The balloon can include a one-way valve or septum in the base portion, through which a filling needle is inserted into a cavity of the balloon. The balloon can be filled with a fluid to expand the balloon and fix the balloon within the patient's body. The balloon can be filled with a hardening material to assist in fixing the balloon in place and occluding the blood vessel. The balloon can include anchoring structure on its outer surface to assist in the fixing the location of the balloon. The delivery device and needle can be detached and withdrawn from the balloon, allowing the septum to close and seal the balloon, leaving the balloon fixed within the body vessel.

23 Claims, 2 Drawing Sheets

Occlusion Balloon

CROSS REFERENCE TO RELATED APPLICATIONS

This application claims the benefit of U.S. Provisional Patent Application No. 61/746,324 filed Dec. 27, 2012, the content of which is hereby incorporated by reference in its entirety.

BACKGROUND

The present invention relates to occlusion balloons and, in particular, to a device for filling an occlusion balloon.

Various ways are used for vascular occlusion procedures to treat, for example, sacular aneurysms and sinus fistulas during therapeutic embolization of a peripheral or cerebral blood vessel. Some types of occlusion devices include balloons, plugs, coils, and particles. A balloon can be delivered and installed to a location in the vasculature. An occlusion plug can be installed within the vasculature at the desired location for the occlusion to limit the blood flow through the desired vessel. Similarly, a coil can be installed to promote clotting in the location of the desired occlusion. Particles can be delivered to the desired occlusion location to similarly promote clotting and limiting of blood flow. One type of particle can be a relatively liquid material that hardens and fills the occlusion site.

However, improvements can be made, and there is a need for an occlusion device that can be reliably and effectively delivered to provide occlusion to a blood vessel.

SUMMARY

A system for occluding a body vessel is provided, the system comprising: a tubular delivery device having a proximal and distal end and a lumen extending therebetween; a detachable balloon detachably mounted to the distal end of the tubular delivery device; a one-way valve disposed at a proximal end of the detachable balloon; and a filling tube having an opening at a distal end thereof, the filling tube extending through the delivery device lumen with the filling tube distal end extending through the one-way valve and into the detachable balloon.

In another form, the system further comprises a threaded connection between the balloon and the delivery device.

In another form, wherein the balloon includes a base portion and the valve is disposed in the base portion.

In another form, the balloon includes attachment structure around its outer surface.

In another form, the attachment structure comprises a stent structure.

In another form, the attachment structure comprises a plurality of channels extending along the outer surface.

In another form, the attachment structure comprises a roughened outer surface.

In another form, the filling tube comprises a needle.

In another form, the system further comprises a fluid disposed within a cavity defined by the balloon.

In another form, the fluid comprises a hardening material.

In yet another form, an occlusion balloon apparatus is provided comprising: an expandable balloon including a base portion having an attachment structure for attaching to a delivery device, the balloon further including an expandable body portion defining an expandable cavity therein; a one-way valve disposed in the base portion arranged for receiving a filling tube therethrough into the balloon cavity and limiting fluid within the cavity from escaping; and an anchoring structure extending about an outer surface of the balloon for fixing the balloon to a wall of a body vessel in response to expansion of the balloon.

In another form, the valve includes a flap portion arranged to pivot into the cavity.

In another form, the anchoring structure comprises a plurality of stent rings.

In another form, the anchoring structure comprises a plurality of channels defining indentation in the body portion of the balloon.

In another form, the expandable body portion comprises silicone, rubber, or ePTFE.

In yet another form, a method for delivery an occlusion balloon to a body vessel is provided, the method comprising: inserting, into a patient's body, a delivery device having an expandable balloon detachably mounted thereto, the balloon including a one-way valve having a filling tube extending therethrough and into a cavity defined by the balloon; delivering the balloon to a body vessel; injecting a fluid into the balloon cavity through the needle; expanding the balloon into engagement with a wall of the body vessel; detaching the balloon from the delivery device; withdrawing the needle from the one-way valve; and removing the delivery device and the needle from the patient's body.

In another form, the step of detaching the balloon comprises rotating the delivery device relative to the balloon to detach the balloon.

In another form, the fluid comprises a hardening material.

In another form, the method further comprises expanding the balloon across two blood vessels.

In another form, an outer surface of the balloon includes an anchoring mechanism for fixing the location of the balloon within the body vessel.

DETAILED DESCRIPTION

Figure 1:
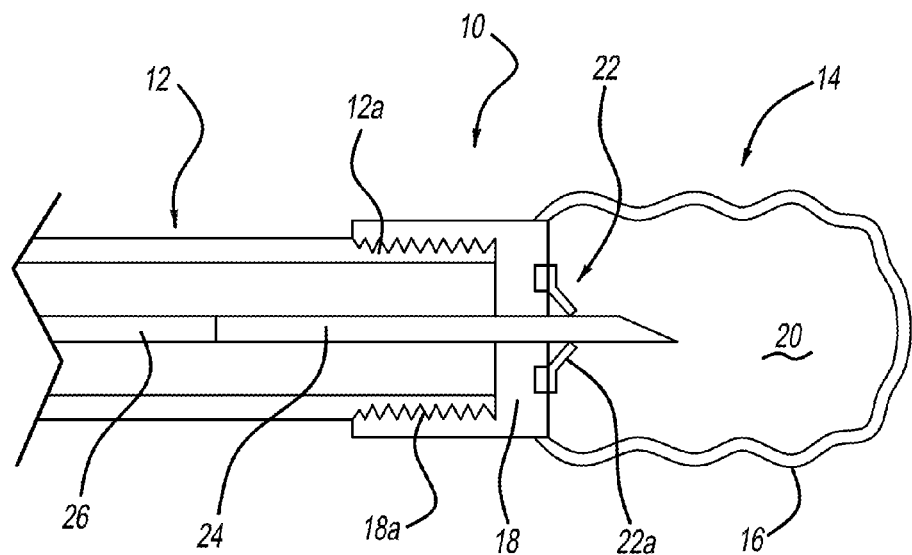
FIG. 1 is a side view of a delivery system for an occlusion balloon.

Referring now to the drawings, FIGS. 1-x illustrate a system 10 for delivering a vascular occlusion balloon. The system includes a delivery catheter 12 with a detachable balloon 14 mounted to a distal end of the catheter 12.

With reference now to FIG. 1, the balloon 14 can include an inflatable body portion 16 attached to a base portion 18. The body portion 16 defines an interior cavity 20 that is configured to be filled with a suitable material to inflate the balloon to a desired size for occluding a body vessel.

The balloon 14 can further include a one-way valve or septum 22. The septum 22 can include one or more flap portions 22a for allowing a needle 24 to be inserted into the cavity 20 for filling the balloon with the desired material to inflate the balloon.

The needle 24 can be attached to a cannula 26 that extends through a lumen 28 of the catheter 12. The needle 24 and cannula 26 include a passageway through which the desired material is delivered toward the balloon. In one form, the needle 24 and cannula 26 can be integrally formed, such that the cannula 26 has a needle 24 at its distal tip. For purposes of discussion, the needle 24 and cannula 26 will be described as separate components; however, it will be appreciated that references to the needle 24 and cannula 26 can likewise apply to a single component having similar structure.

In another approach, the catheter 12 could have the needle 24 integrally formed at the distal end of the catheter 12.

The base portion 18 of the balloon 14 can include an attachment mechanism or threads 18a. The threads 18 can correspond to threads 12a that are disposed at the distal end of the catheter 12. The engagement between the threads 12a and 18a attaches the balloon 14 to the catheter 12 in a robust fashion to limit instances where the balloon 14 can become detached during delivery to the occlusion location.

Figure 2:
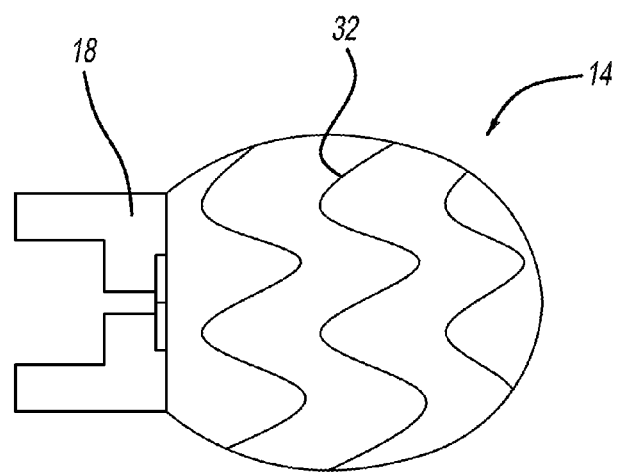
FIG. 2 is a side view of a first embodiment of the occlusion balloon.
Figure 3:
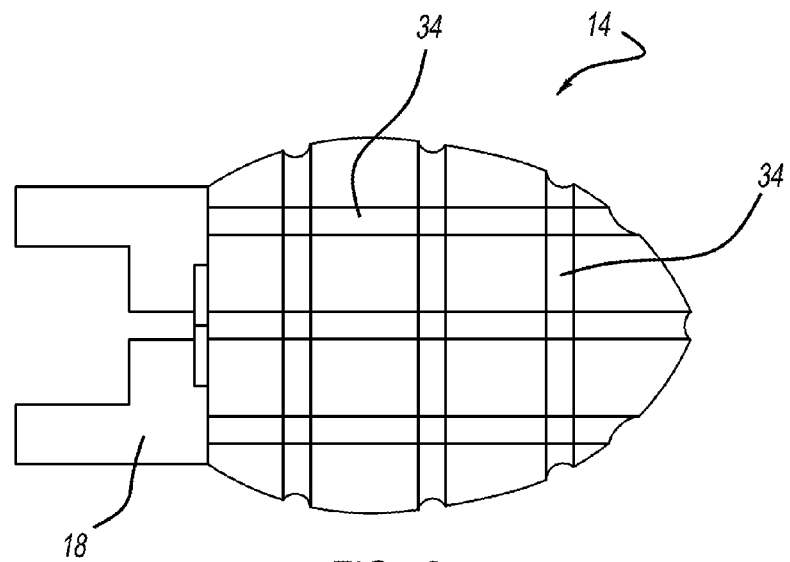
FIG. 3 is a side view of a second embodiment of the occlusion balloon.

With reference to FIGS. 2 and 3, the balloon 14 can include an anchoring structure 30 disposed on the body portion 16 for limiting migration of the balloon once it has been deployed within the vasculature.

With reference to FIG. 2, in one form, the anchoring structure 30 can be in the form of stents 32, or the like, surrounding the outer surface of the body portion 16. The stents 32 can be any type of stent structure known in the art. The stents 32 can have a generally sharp surface for promoting tissue ingrowth when the balloon 14 is expanded against the wall of the blood vessel. In one form, the stents 32 can be in the form of a spiral coil or mesh type structure. The stents 32 are preferably arranged to expand as the balloon 14 is filled.

With reference to FIG. 3, the anchoring structure can be in the form of scoring elements or channels 34 that can extend laterally about the balloon 14, longitudinally along the balloon 14, or both. In another form, the channels 34 could extend at oblique angles relative to each other, or at a transverse angle to the longitudinal direction of the balloon 14. The channels 34 can define indentations 34a in the surface of the balloon 14 to create an undulating out surface, which can limit migration of the balloon after deployment.

In another approach, the surface of the balloon can be roughened, or a coating can be applied, to increase the friction of the balloon 14 relative to the wall of the blood vessel to which the balloon 14 is installed. It will be appreciated that other approaches known in the art for limiting migration of the balloon 14 could also be used, such as barbs or the like.

The balloon 14 can be made from a highly compliant material for installation within a body vessel. For example, the balloon 14 can be made of silicone, rubber, ePTFE, breast implant material, other biocompatible stable compliant material, or the like.

The balloon 14 can be inflated with a variety of materials to increase the size of the balloon 14 during installation for occluding the blood vessel. For example, the balloon 14 can be inflated with water, saline, a contrast agent, silicone oil, or other biocompatible solution known in the art for inflating balloons with the body.

In one approach, the balloon 14 can be filled with a material that hardens over time. The hardening material can be injected into the balloon 14 to inflate the balloon 14 similar to a known liquid material. The balloon 14 can become inflated to install the balloon 14 at the occlusion site, and the hardening material can then harden to set the shape of the balloon 14. Thus, the balloon 14 can be adapted to fit and plug a variety or tortuous anatomy shapes once inflated and limit the balloon 14 from changing its shape after installation.

Having described the general structure of the occlusion system 10, the delivery and use of the balloon 14 will now be described.

Figures 4, 5, 6:
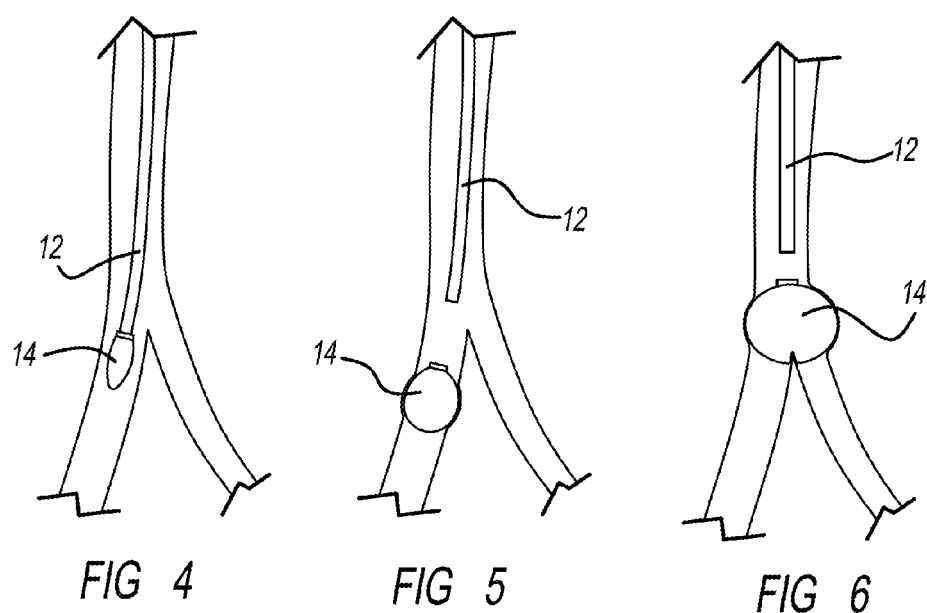
FIG. 4 is a schematic view of the delivery system delivering the balloon within a body vessel.
FIG. 5 is a schematic view of the balloon having been installed within the body vessel.
FIG. 6 is a schematic view of the balloon having been installed in an alternate location within the body vessel.

With reference to FIGS. 1 and 4-6, the delivery catheter 12 having the balloon 14 releasably attached thereto can be delivered into the patient's vasculature in a manner known in the art, such as a percutaneous method, minimally invasive technique, Seldinger method, or the like. The delivery catheter 12 having the balloon 14 attached can be navigated through the tortuous vasculature toward the target site where occlusion is desired, as shown in FIG. 4.

Once the balloon 14 has been delivered to the target site, the balloon 14 can be filled with fluid through the cannula 26 and needle 24 to inflate the balloon 14 until it occludes and satisfactorily presses against the vessel wall to fix it in the place. The anchoring structure 30, described above, will assist in fixing the balloon 14 in place and limiting migration of the balloon 14 from the desired location for occlusion.

Once the balloon 14 has been fixed in place, the delivery catheter 12 can be detached from the balloon 14 by rotating the catheter 12 in the direction to become unthreaded from the base 18. The delivery catheter 12 can then be withdrawn from the balloon 14 leaving the balloon 14 in its fixed occlusion position.

Additionally, the needle 24 and cannula 26 can be withdrawn to withdraw the needle 24 from the balloon cavity 20 through the septum 22. The septum 22 will close as the needle 26 is withdrawn, thereby sealing the cavity 20 of the balloon 14. The balloon 14 will thereby retain the fluid that was injected to inflate the balloon 14.

With the balloon 14 detached from the delivery catheter 12 and the needle 24, the delivery catheter 12 and needle 24 can be withdrawn from the patient's body, as shown in FIG. 5.

In one form, the catheter 12, cannula 26, and needle 24 are directly or indirectly coupled together. Thus, rotating the catheter 12 to detach it from the balloon 14 will cause the cannula 26 and needle 24 to rotate along with the catheter 12. In this approach, the needle 24 will rotated relative to the septum 20 as the catheter 12 is unthreaded from the balloon 14. Additionally, as the catheter 12 and balloon 14 are de-coupled by unthreading, the catheter 12 and needle 24 will be slightly withdrawn in response to the relative rotation between the threads 18a and 12a.

With reference to FIG. 6, the balloon 14 can installed across an additional branch of the vasculature, or sidebranch. The balloon 14 can be installed in a manner similar to the above in this approach. The inflation of the balloon 14 will cause the balloon 14 to become fixed and both branches to become occluded. The installation across a sidebranch can assist in fixing the balloon 14 within the veseel.

The above description of installing the balloon 14 also applies to instances where a hardening material is injected into the balloon 14 to inflate it. The needle 24 and catheter 12, after injecting the balloon 14 with hardening material, are preferably withdrawn prior to the material becoming hardened to limit instances of pulling the balloon 14 away from its desired location. However, depending the needs of the user, the catheter 12 can remain attached to the balloon while the material hardens to assist in fixing the balloon 14 in the desired location. The risk of migration of the balloon 14 can be counteracted by a more robust fixing of the balloon 14 to the vasculature.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A system for occluding a body vessel, the system comprising: a tubular delivery device having a proximal and distal end and a lumen extending therebetween; a detachable balloon rotatably detachably mounted to the distal end of the tubular delivery device by a thread connection; a one-way valve disposed at a proximal end of the detachable balloon; and a filling tube having an opening at a distal end thereof, the filling tube extending through the delivery device lumen with the filling tube distal end in fluid communication with a cavity defined by the balloon.

2. The system of claim 1, wherein the balloon includes a base portion and the valve is disposed in the base portion.

3. The system of claim 1, wherein the balloon includes attachment structure around its outer surface.

4. The system of claim 3, wherein the attachment structure comprises a stent structure.

5. The system of claim 3, wherein the attachment structure comprises a plurality of channels extending along the outer surface.

6. The system of claim 3, wherein the attachment structure comprises a roughened outer surface.

7. The system of claim 1, wherein the filling tube comprises a needle.

8. The system of claim 1 further comprising a fluid disposed within the cavity defined by the balloon.

9. The system of claim 8, wherein the fluid comprises a hardening material.

10. The system of claim 1, wherein the delivery device and the filling tube are coupled together such that the filling tube will rotate along with the delivery device when the delivery device is rotated.

11. The system of claim 1, wherein the filling tube extends through and beyond the one-way valve and into the detachable balloon.

12. An occlusion balloon apparatus comprising: a tubular delivery device; an expandable balloon including a base portion having an attachment structure for rotatably attaching to the tubular delivery device, the balloon further including an expandable body portion defining an expandable cavity therein, and wherein the attachment structure is a thread; a one-way valve disposed in the base portion arranged for limiting fluid within the cavity from escaping; an anchoring structure extending about an outer surface of the balloon for fixing the balloon to a wall of a body vessel in response to expansion of the balloon; and a filling tube for being coupled to the tubular delivery device, the filling tube extending through and beyond the one-way valve and into the balloon cavity.

13. The apparatus of claim 12, wherein the valve includes a flap portion arranged to pivot into the cavity.

14. The apparatus of claim 12, wherein the anchoring structure comprises a plurality of stent rings.

15. The apparatus of claim 12, wherein the anchoring structure comprises a plurality of channels defining indentation in the body portion of the balloon.

16. The apparatus of claim 12, wherein the expandable body portion comprises silicone, rubber, or ePTFE.

17. The device of claim 12, further comprising a delivery device rotatably detachably coupled to the attachment structure of the balloon, wherein the delivery device and the filling tube are coupled together such that the filling tube will rotate along with the delivery device when the delivery device is rotated.

18. A method for delivering an occlusion balloon to a body vessel, the method comprising: inserting, into a patient's body, a delivery device having an expandable balloon rotatably detachably mounted thereto, the balloon including a one-way valve, wherein a needle extends through a lumen of the delivery device and is in fluid communication with a cavity defined by the balloon; delivering the balloon to a body vessel; injecting a fluid into the balloon cavity through the needle; expanding the balloon into engagement with a wall of the body vessel; detaching the balloon from the delivery device by rotating the delivery device relative to the balloon, thereby, decoupling a thread connection between the delivery device and the expandable balloon; withdrawing the needle from the one-way valve; and removing the delivery device and the needle from the patient's body.

19. The method of claim 18, wherein the fluid comprises a hardening material.

20. The method of claim 18 further comprising expanding the balloon across two blood vessels.

21. The method of claim 18, wherein an outer surface of the balloon includes an anchoring mechanism for fixing the location of the balloon within the body vessel.

22. The method of claim 18, wherein the delivery device and the needle are coupled such that the needle and delivery device are rotated, withdrawn, and removed together.

23. The method of claim 18, wherein the needle extends through and beyond the one-way valve.

* * * * *